United States Patent [19]

Belgorod

[11] 4,279,474
[45] Jul. 21, 1981

[54] SPECTACLE LENS HAVING CONTINUOUSLY VARIABLE CONTROLLED DENSITY AND FAST RESPONSE TIME

[76] Inventor: Barry M. Belgorod, 450 E. 63 St., New York, N.Y. 10021

[21] Appl. No.: 133,929

[22] Filed: Mar. 25, 1980

[51] Int. Cl.³ .............................. G02F 1/133
[52] U.S. Cl. ................... 350/331 R; 350/334; 350/332; 351/41; 351/44
[58] Field of Search ............... 350/331 R, 334, 332, 350/347 E; 351/41, 44; 250/205

[56] References Cited

U.S. PATENT DOCUMENTS

| | | | |
|---|---|---|---|
| 3,815,982 | 6/1974 | Wagensonner | 350/331 R |
| 3,886,014 | 5/1975 | Bayer | 350/335 X |
| 3,942,270 | 3/1976 | Hoyt et al. | 350/334 X |
| 3,975,726 | 8/1976 | Kawakami | 350/332 X |
| 4,021,935 | 5/1977 | Witt | 350/331 R X |
| 4,037,929 | 7/1977 | Bricot et al. | 350/331 R X |
| 4,039,803 | 8/1977 | Harsch | 350/331 R X |
| 4,066,335 | 1/1978 | Courtney et al. | 350/331 R X |
| 4,106,217 | 8/1978 | Witt | 350/331 R X |
| 4,181,408 | 1/1980 | Sendees | 351/41 X |
| 4,190,330 | 2/1980 | Berreman | 350/331 R |

OTHER PUBLICATIONS

Kaneko et al., "Liquid Crystal Television Display", *Proceeding of the S.I.D.*, vol. 19/2, pp. 49–54, Apr. 1978.

*Primary Examiner*—Edward S. Bauer
*Attorney, Agent, or Firm*—Schwartz & Weinrieb

[57] ABSTRACT

A spectacle lens comprises a liquid crystal layer and electrode assembly sandwiched between a pair of identically curved glass plates and layers of polarization material on the outer surfaces of the plates. The optical density of the lens is controlled by applying across the electrodes variable duty cycle voltage pulses having a magnitude greater than a threshold voltage of the liquid crystal layer and a frequency at least as great as the critical flicker fusion frequency of the eye. The duty cycle of the pulses is controlled in response to ambient light intensity measured by a photocell. In order to reduce response time and increase operating lifetime of the liquid crystal layer, tir-level (+V, 0, −V) rather than bilevel (+V, 0) pulses may be applied to the liquid crystal electrodes.

8 Claims, 17 Drawing Figures

SPECTACLE LENS HAVING CONTINUOUSLY VARIABLE CONTROLLED DENSITY AND FAST RESPONSE TIME

TECHNICAL FIELD

The present invention relates generally to variable density lenses and more particularly toward fast response time variable density lenses wherein density is controlled as a function of ambient light intensity.

BACKGROUND ART

The limits of luminance for reading comfort are known based upon experimentation to fall within the range of 10 to 100 milliLamberts (mL). This is the approximate equivalent luminance of white paper under 10 to 100 foot candles of illumination. In order to limit the amount of light impinging on the eye to the 10 to 100 mL range, there exists a need for spectacle lenses that remain maximally transmissive below 100 mL and become increasingly dense above the 100 mL illumination level. Previous attempts to design a lens for this purpose have lead to the development of photochromic (also called phototropic or identified under the trademark PHOTOGRAY) glass that darkens when exposed to light but regains its original transparency a period of time after the light is removed. Photochromic glass has a relatively slow response time. At least 60 seconds are required for photochromic glass to darken to 75% of its maximum density with full darkening requiring at least 5 minutes. Even when fully darkened, the density of photochromic glass is less than that of most conventional sun-glasses. An even more significant drawback of photochromic glass is that recovery to initial transparency is very slow; recovery is only 50% in 5 minutes to 75% in 20 minutes. The sight of an individual entering a dark room from high intensity ambient lighting can thus be temporarily blocked during the recovery period. Furthermore, maximum density of the prior art device is inversely proportional to temperature and it is mainly sensitive to wavelengths outside the range of human vision.

There exists a present need, therefore, for a lens that approaches the characteristics of "ideal sunglasses", that is, one which has fast response time over a wide range of optical densities. The need goes beyond that of simple comfort or convenience. Strict control of light levels incident on the eye is often required for physiologic reasons, i.e., tape-toretinal degenerations, macular disease or for therapeutic reasons, i.e., ocular inflammatory states, post-operative cataract surgery or sector iridectomies.

One object of the present invention, therefore, is to provide a variable density lens that has a faster response time than the prior art photochromic lens.

Another object is to provide a fast response time variable density lens that is controlled automatically in response to ambient light intensity in the visible range.

Another object is to provide a spectacle lens having a density that is continuously variable within a wide density range in response to ambient light intensity and has a short response time to change of ambient light intensity.

DISCLOSURE OF INVENTION

A spectacle lens, in accordance with the invention, comprises a layer of liquid crystal material sandwiched between a pair of identically curved glass lenses. Opposite outer surfaces of the liquid crystal layer are in contact with transparent electrically conductive electrodes. Polarized material is laminated on the outer surfaces of the two lenses whereby the density of the assembly is controlled as a function of voltage greater than a threshold voltage applied to the electrodes.

A control voltage is applied to the electrodes in the form of voltage pulses having a magnitude greater than the threshold voltage and a frequency at least as great as the critical flicker fusion frequency of the human eye. The duty cycle of the pulses is controlled as a function of ambient light intensity measured by a photocell to maintain light passing through the lens at a comfortable luminous level.

The pulse generator comprises a pair of mutually triggered monostable multivibrators having an on-period controlled by the ambient light responsive resistor and an off-period controlled by a fixed or variable calibration resistor. An optional driver is provided for converting the bilevel (+V, 0) output of the pulse generator to tri-level (+V, 0, −V) pulses to improve the response time of the liquid crystal layer.

Liquid crystal materials have been used in the past for controlling light transmission. It has been proposed, for example, in U.S. Pat. Nos. 4,701,912 and RE. 29,684 to incorporate liquid crystal material within the flat transparent plate of a welding helmet eyepiece. The eyepiece is normally maintained at maximum transparency and is controlled to switch to minimum transparency in response to initiation of a welding arc. There is no continuous modulation of the transparency as is required in spectacles. Furthermore, the eyepiece, being flat, cannot function as a therapeutic lens of the type required in spectacles.

Continuous modulation of transparency or transmissivity (density) of a liquid crystal device by varying the magnitude of a voltage applied across the liquid crystal electrodes is disclosed in U.S. Pat. No. 4,066,335. Analog voltage control, however, tends to be unstable and does not lend itself to miniaturization using integrated circuits. Furthermore, calibration is relatively difficult since analog voltage level measuring circuitry is required. The type of control taught in that patent is designed to be applied in relatively bulky imaging systems in xerographic copying machines but is impractical for application in spectacles. Furthermore, the liquid crystal layer in the patent is planar in the transmissive device and therefore would not be applicable to a therapeutic lens.

Another object of the invention, therefore, is to provide a therapeutic lens having continuously variable controlled density.

Still another object of the invention is to provide a variable density lens that is stable, easily calibrated and subject to miniaturization using digital integrated circuitry.

BEST MODE FOR CARRYING OUT THE INVENTION

Figure 1:
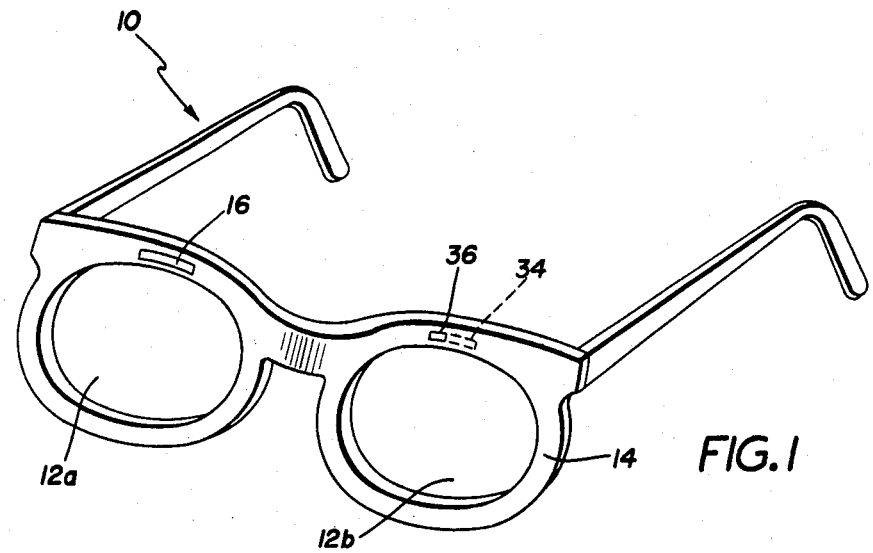
FIG. 1 is a perspective view of a pair of spectacles equipped with the variable density lens of the present invention.

Referring to FIG. 1, a pair of spectacles 10 comprises a frame 14 carrying a pair of substantially identical variable density lenses 12a, 12b each containing a liquid crystal layer controlled to alternate rapidly between maximum and minimum optical densitites at a frequency higher than the critical flicker fusion frequency of the human eye. The duty cycle of the alternation varies as a function of ambient light intensity measured by photodetector 16 to provide an average or integrated density that appears constant to maintain a comfortable level of luminance on the eye.

The concept of controlling the optical density of liquid crystal lenses 12a, 12b is based upon the Plateau-Talbot law which states that above the critical flicker fusion frequency (which varies, according to the Ferry-Porter law, from 10 Hz at low stimulus intensities to an absolute maximum of 45 Hz), the eye averages the effects of intermittent stimuli on a linear basis, i.e., the apparent brightness of illumination switched on and off at a frequency greater than the critical flicker fusion frequency is equal to the portion of time spent in the on state relative to the total cycle (i.e., the "duty cycle") weighted according to the intensities of the on and off states. On-off intensities of 100% and 0% of equal duration would thus be averaged by the eye to appear as a constant intensity of 50%.

The Weber-Fechner law states that the just noticeable difference by the eye of change in illumination intensity is constant for a given intensity, or $(\Delta I/I) = K$, where I is illumination intensity. For luminances of $10^{-1}$ to $10^4$ mL, this fraction K is virtually constant at a value of approximately 0.02. Thus, the eye is not capable of responding to fractional changes in light intensity of less than 2% in this range.

Based on the above data, the density of lenses 12a, 12b is controlled to oscillate between maximum and minimum densities (ideally 100% and 0%) at a duty cycle resolution of about 0.02 within the range of $10^{-1}$ to $10^4$ mL.

In their simplest form, nematic liquid crystal light modulators are formed of a pair of flat glass plates sandwiching a 10 to 20 microns thick layer of a nematic liquid crystalline composition provided in the twisted nematic state with a 90° twist, as shown in U.S. Pat. No. 3,731,986, for example, and described in Schadt, et al., *Voltage Dependent Optical Activity of A Twisted Nematic Liquid Crystal*, Applied Physics Letters, Volume 18, Number 4 (1971), which will rotate the plane of polarization of linearly polarized light 90°. The flat glass plates are coated with very thin layers of a transparent electrical conductor such as $SnO_2$ and/or $In_2O_3$ applied by either thin film pyrolysis or vacuum deposition. An applied voltage above a threshold voltage for the liquid crystal composition will cause the liquid crystal molecules to align themselves either parallel or perpendicular to the applied field depending on the dielectric anisotropy of the compound. For positive dielectric anisotropy, the molecules tend to align themselves perpendicular to the electrode surfaces (i.e., parallel to the applied field). The electrodes are grooved with one micron diamond paste to achieve uniform parallel alignment of the surface molecules with respect to each other and to the electrode surfaces in the resting phase. If the electrodes are assembled with the groove axes at 90° to each other, the liquid crystal molecules assume a helical orientation in the resting state which is disrupted when the applied voltage $V_A$ is greater than or equal to the critical voltage $V_c$ such that the molecules tend to align mainly perpendicular to the electrodes.

At rest, the helical configuration will effect a 90° rotation of the plane polarized light. If crossed polarizers are positioned on either side of the cell with their respective polarizing axes parallel to the axes of grooving on their adjacent electrodes, maximal light transmission will occur in the resting state ($V_A = 0$). Minimal transmission of light will occur when $V_A \geq V_c$ as the perpendicular orientation of the liquid crystal molecules will not significantly rotate plane polarized light. The net effect on incident light is that of crossed polarizers with axes 90° apart. The apparent optical density of the lens, in accordance with the invention, is a function of the relative time periods of the lens maintained in the light and dark states at frequencies above the critical flicker fusion frequency of the eye.

Figure 2:
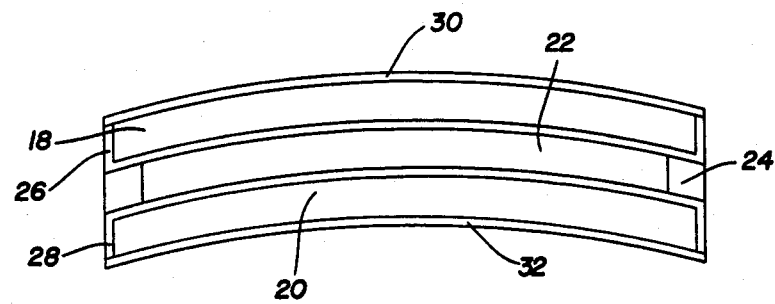
FIG. 2 is a cross sectional view of the variable density lens showing its internal structure.

Referring now to FIG. 2, an ophthalmic lens 12, in accordance with the invention, comprises first and second substantially identical curved lenses 18 and 20 sandwiching a layer 22 of twisted nematic liquid crystal 22 retained within the lenses by a resilient seal 24. The inner surfaces of the lenses 18 and 20 are coated with electrically conductive transparent layers 26, 28 in the conventional manner for applying a polarization altering electric field across the liquid crystal layer 22. Optional thin layers (not shown) of sintered or fused glass or silicon oxide may be coated on the inner surfaces of electrodes 26, 28 as taught in U.S. Pat. No. 3,700,306 to extend liquid crystal operating lifetime. Opposite outer surfaces of the lenses 18 and 20 are laminated with layers 30 and 32 of polarizing material with axes parallel to the adjacent electrodes grooving axes. The polarizing sheets both enable the lens 12 to operate in a variable density mode as described above and prevent shattering.

Referring again to FIG. 1, the lenses 12a and 12b are electrically connected to integrated circuitry 34 preferably located within the frame 14 or earpiece 15. A battery 36 for energizing the integrated circuitry 34 and supplying the control voltage to be applied across the lenses 12 is also preferably located within the frame 14 or earpiece 15. The battery voltage must be greater than the critical voltage of the liquid crystal material 22 and also must be appropriately matched to the family of integrated circuitry provided as 34. The integrated circuitry 34 is preferably of the CMOS family or other high impedance, low current consumption family to minimize battery drain.

Also located within frame 14 or nosepiece 17 is a photodetector 16 which measures ambient light intensity to control the duty cycle of voltage pulses applied via circuit 34 to the two lenses 12a and 12b in the manner discussed below in more detail. Wiring interconnecting the lenses 12a, 12b, photodetector 16, circuitry 34 and battery 36 is not shown in FIG. 1 for simplicity.

The wiring is preferably, however, formed within the body of the frame 14 to contact the exposed electrode surfaces of the edge of the lens and to reduce the likelihood of breakage.

Figure 3:
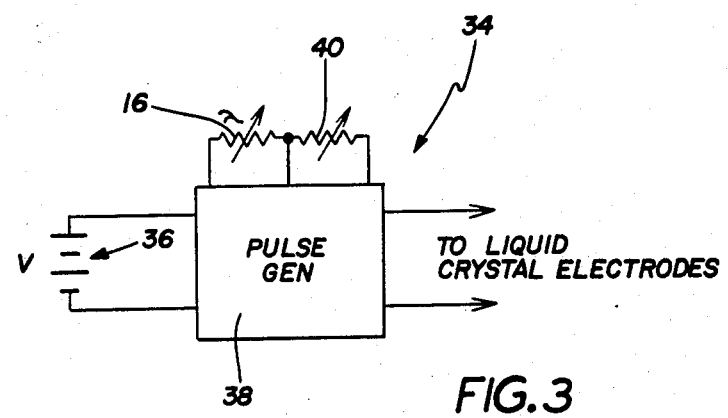
FIG. 3 is a simplified block diagram showing circuitry for controlling the density of the lens as a function of ambient light intensity.

Referring now to FIG. 3, the circuitry 34 for supplying variable duty cycle pulses at a magnitude greater than the threshold level of the liquid crystal material 22 and at a frequency at least as great as the critical flicker fusion frequency of the eye comprises a variable duty cycle pulse generator 38 that is energized by the battery 36 and controlled to generate pulses having a duty cycle that is variable as a function of the value of photodetector 16 and a calibration resistor 40. Calibration resistor 40 and photodetector 16 are selected such that below the maximum of the range for comfortable ambient light intensity the minimum transmissive phase of the duty cycle should be less than the just noticeable difference (J.N.D.) or <0.02 (by the Weber-Fechner and Plateau-Talbot laws) and in maximum ambient lighting the maximum transmissive phase of the duty cycle should be <0.02. The lenses will therefore appear maximally dark in bright light and maximally transmissive in dim and comfortable light. The frequency of the pulse train cycle consisting of successive on and off periods (+V, 0) is selected to be greater than 10 Hz and preferably greater than 45 Hz to provide the appearance to the eyes of constant flicker free illumination through the lenses. Based on these criteria, I have determined that maximum cycle period should not exceed 22 to 100 miliseconds, with longer cycle periods tolerated at lower light levels where the critical flicker fusion frequency is at the low end of the scale. Thus, in summary, the pulses generated by generator 38 as a function of ambient light intensity have the following characteristics:

Absolute Maximum pulse width = 100 milliseconds
Minimum duty cycle <0.02
Maximum duty cycle >0.98

Figure 4:
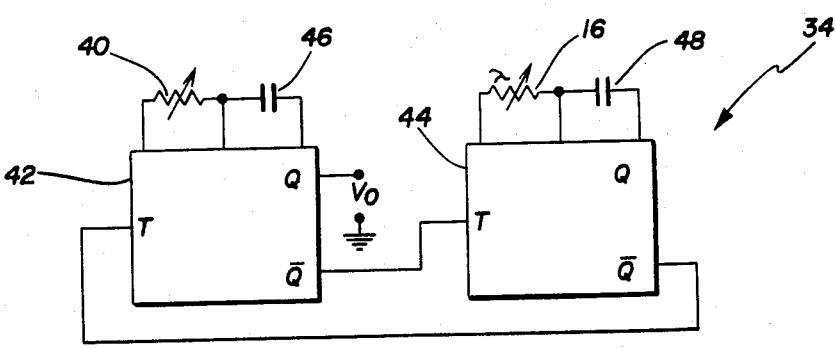
FIG. 4 is a more detailed circuit diagram of the pulse generator of FIG. 3.

Referring to FIG. 4, one embodiment of pulse generator 38 comprises first and second, conventional monostable multivibrators 42 and 44, mutually interconnected with each other to independently control the on (+V) period and off (0) period of an output pulse train. Each of the monostable multivibrators 42 and 44 is a standard toggle flip-flop operated in a multivibrator mode, wherein a positive voltage applied to is toggle input T causes the normally low (0) voltage at output Q to switch to a high (+V) voltage for a time period predetermined by the values of corresponding resistors 16 and 40 and capacitors 46 and 48. The complementary output $\overline{Q}$ of flip-flop 42 is connected to the toggle input T of flip-flop 44. The complementary output $\overline{Q}$ of flip-flop 44 in turn is connected to the toggle input T of flip-flop 42. The output $V_o$ of circuit 34 is obtained at the flip-flop 42 output terminal Q.

Figure 6A:
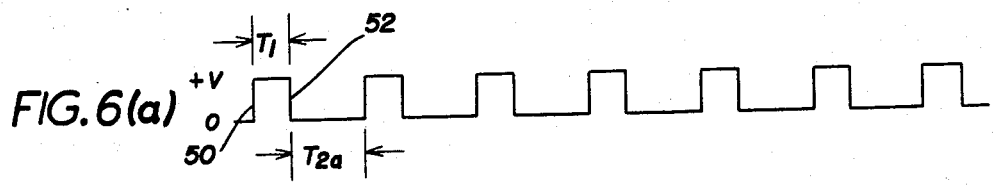
FIGS. 6(a) and 6(b) are waveforms useful for explaining the operation of the circuit of FIG. 4.

Referring to FIGS. 4 and 6(a), upon energization of the pulse generator 34 by battery 36 (FIG. 3), and assuming that the outputs Q of flip-flops 42 and 44 are both initially at zero, and further assuming that the first flip-flop 42 is stabilized at the zero output level prior to stabilization of flip-flop 44 (this condition can be ensured using conventional power on reset or reset delay circuitry), the flip-flop 42 is triggered at input terminal T by the output $\overline{Q}$ of flip-flop 44 as $\overline{Q}$ makes an initial transition between the zero and +V voltage levels during turn-on. In response, the output Q of flip-flop 42 switches from zero to +V as illustrated by waveform portion 50 in FIG. 6(a). After the time period $T_1$ determined by the values of calibrating resistor 40 and capacitor 46 connected in circuit with flip-flop 42, the output Q of the flip-flop 42 switches to zero volts as shown by 52 in the waveform of FIG. 6(a). The corresponding positive transition of $\overline{Q}$ of flip-flop 42 triggers flip-flop 44 which causes flip-flop 44 complementary output Q to switch to zero volts for a predetermined time $T_{2a}$ determined by light responsive resistor (photodetector) 16 and capacitor 48. The Q output of flip-flop 42 is also at zero volts during this period, as shown in FIG. 6(a). At the end of the period $T_{2a}$, the $\overline{Q}$ output of flip-flop 44 switches to +V, again triggering flip-flop 42 and initiating another cycle.

Figure 6B:
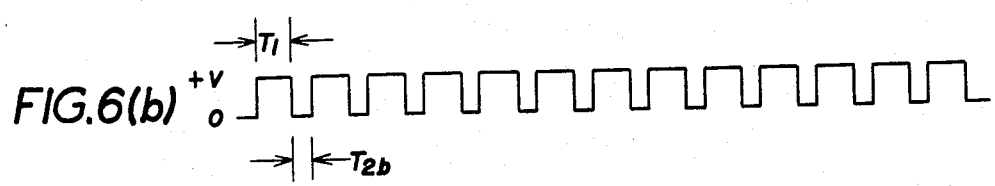

The +V period $T_1$ of the pulse generator 34 is constant based upon the calibration setting of the resistor 40. In practice, resistor 40 may be fixed at a predetermined calibration level to eliminate the requirement of a calibration potentiometer on spectacles frame 14. The zero voltage time $T_2$, however, is variable as illustrated in FIG. 6(a) and 6(b), showing, respectively, pulse trains generated during low ambient light intensity and high ambient light intensity. The pulse train shown in FIG. 6(a) causes the lens 12 to have low density (maximum light transmission) and is designed as aforementioned to have a maximum duty cycle of less than 0.02. The waveform of FIG. 6(b) causes the lens 12 to have a high density (minimum light transmission) and is designed to have a minimum duty cycle greater than 0.98.

Figure 5:
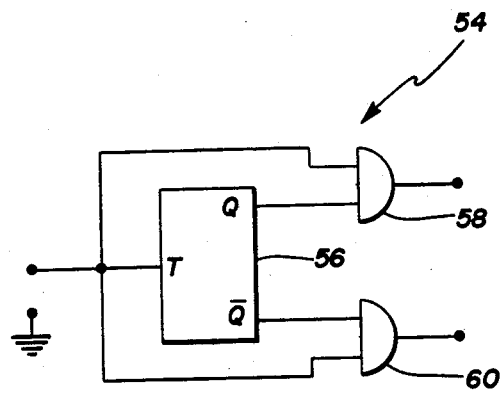
FIG. 5 is a diagram of a circuit for converting the pulses generated by the circuit of FIG. 4 into corresponding bidirectional pulses to improve response time of the variable density lens.

As discussed above, a particular advantage of the variable density lens and driving circuitry of the present invention over the prior art photochromic lens is in its substantially faster response time in both the lightening and darkening modes (on the order of milliseconds as opposed to minutes in the prior art photochromic lens). To even further improve the response time and to also increase the lifetime of the lens 12, the output of pulse generator 38 may be supplied to a driver circuit 54 shown in FIG. 5 which converts the bilevel (+V, 0) pulses to alternating polarity, trilevel (+V, 0, −V) pulses and is capable of handling a variable duty cycle waveform. The principle of reducing the response time of a liquid crystal device by pulse polarity reversal using bilevel pulses of fixed frequency is described in U.S. Pat. No. 4,161,653. In accordance with the present invention, the output of the pulse generator 34 is supplied to the toggle input T of a toggle flip-flop 56. The Q and $\overline{Q}$ outputs of flip-flop 56 are supplied to one input of each of AND gates 58 and 60. The remaining inputs of the two AND gates 58, 60 are connected to the toggle input T of flip-flop 56.

Figure 7A:
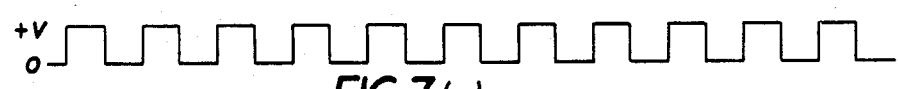
FIGS. 7(a)–7(j) are waveforms useful for explaining the operation of the circuit of FIG. 5.
Figure 7B:
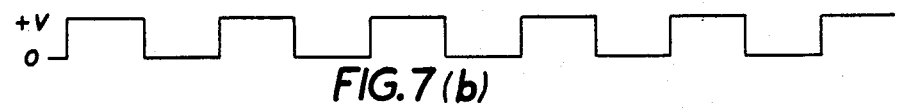
Figure 7C:
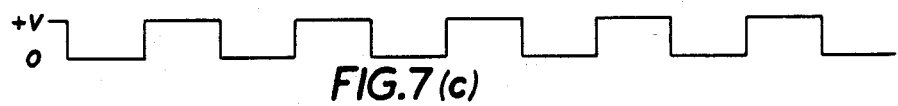
Figure 7D:
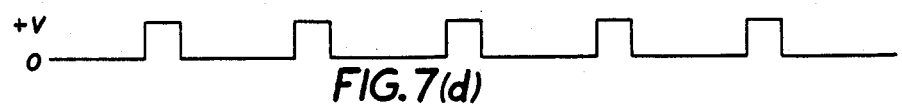
Figure 7E:
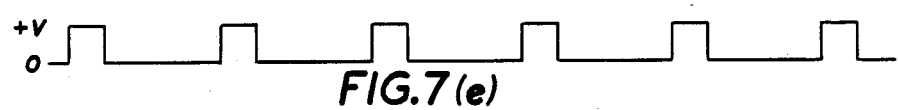
Figure 7F:

The operation of the circuit 54 can be understood with reference to FIG. 7(a)–7(f). Assuming a nominal pulse train shown in FIG. 7(a) produced by generator 34 and applied to toggle input T of flip-flop 56, the output waveforms at Q and $\overline{Q}$ of the flip-flop are shown respectively in FIG. 7(b) and 7(c). The output pulse at Q is logically ANDed at AND gate 58 with the input pulse to provide the waveform shown in FIG. 7(d). Similarly, the $\overline{Q}$ output is logically ANDed at AND gate 60 with the input pulse train to provide the phase shifted waveform of FIG. 7(e). The output of gates 58 and 60 are connected respectively to electrodes 26 and 28 of each of the lenses 12a and 12b. Accordingly, the voltage applied across the liquid crystal material 22, which is the algebraic difference between the waveforms shown in FIGS. 7(d) and 7(e), is shown in FIG. 7(f). Of particular importance, the voltage generated by driver 54 has three levels, +V, 0 and −V, to provide a voltage reversal effect across the liquid crystal material. The duty cycle of the waveform is the ratio of either the positive or negative V period and the total period of each cycle.

Figure 7G:
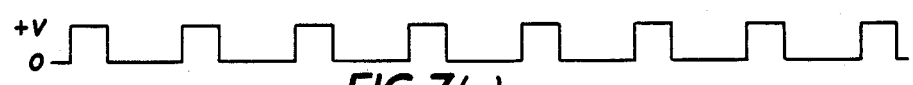
Figure 7H:
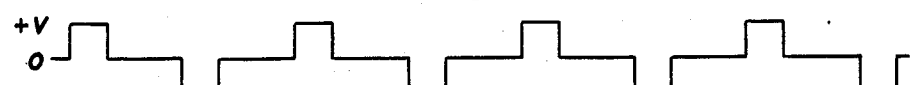
Figure 7I:
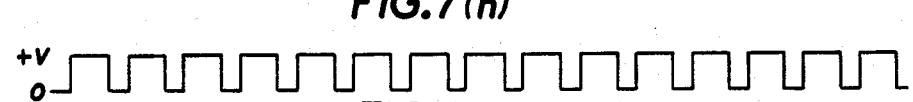
Figure 7J:
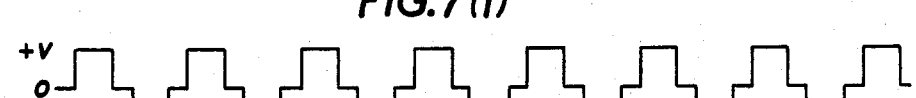

Referring to FIGS. 7(g) and 7(h), the input and output pulse trains with respect to driver circuit 54 are shown wherein the pulse train has a low duty cycle in response to low intensity ambient lighting. The output pulses 7(h) applied across liquid crystal material 22 are bidirectional and have a low duty cycle corresponding to the duty cycle of the pulses in FIG. 7(g). Similarly, FIGS. 7(i) and 7(j) show corresponding waveforms wherein duty cycle is high in response to high intensity ambient lighting. It is understood that in practice the duty cycle will vary continuously between the high and low duty cycles shown in these waveforms for intermediate intensities of ambient lighting measured by photodetector 16.

In this disclosure, there is shown and described only the preferred embodiments of the invention, but, as aforementioned, it is to be understood that the invention is capable of use in various other combinations and environments and is capable of changes or modifications within the scope of the inventive concept as expressed herein.

I claim:

1. A spectacle lens having continously variable density, comprising a liquid crystal means within said lens for controlling light transmission through said lens as a function of an applied voltage, means for applying voltage pulses across said liquid crystal means, said pulses having a magnitude greater than a threshold value of said liquid crystal means and a frequency at least as large as the critical flicker fusion frequency of an eye, and means for controlling the duty cycle of said pulses to maintain the light passing through the lens at a predetermined luminous level.

2. A spectacle lens having a continously variable density as a function of ambient light, comprising a liquid crystal means within said lens for controlling light transmission through said lens as a function of an applied voltage; means for measuring ambient light intensity; generator means for applying voltage pulses across said liquid crystal means, said pulses having a magnitude greater than a threshold value of said liquid crystal means and a frequency at least as large as the critical flicker fusion frequency of an eye; and means responsive to said light measuring means for controlling the duty cycle of said pulses to maintain the light passing through the lens at a predetermined luminous level.

3. The spectacle lens of claim 1 or claim 2, wherein said lens comprises first and second curved lenses, said liquid crystal means being sandwiched between said first and second lenses, transparent electrically conductive electrodes on opposite sides of said liquid crystal means and polarizer means on opposite outer surfaces of said first and second lenses.

4. The spectacle lens of claim 1 or claim 2, including driver means for generating bidirectional pulses synchronized to pulses generated by said pulse generator means, and steering means for supplying said bidirectional pulses respectively to opposite electrodes of said liquid crystal means.

5. The spectacle lens of claim 2, including calibration means for presetting said pulse generator to generate pulses having a predetermined duty cycle at a predetermined ambient light intensity.

6. A variable density spectacle lens, comprising first and second substantially identical curved lenses; liquid crystal means sandwiched between said lenses; transparent, electrically conductive electrode layers on opposite sides of said liquid crystal means; polarizer means on opposite outer surfaces of said first and second lenses, means for applying voltage pulses across said liquid crystal means, said pulses having a magnitude greater than a threshold value of said liquid crystal means and a frequency at least as large as the critical flicker fusion frequency of an eye, and means for controlling the duty cycle of said pulses to maintain the light passing through the lens at a predetermined luminous level.

7. In a spectacle lens having a liquid crystal means located within the optical path of the lens, wherein the density of said liquid crystal means is variable as a function of a voltage greater than a threshold voltage applied across said liquid crystal means, a method of controlling optical density comprising the steps of generating voltage pulses having a magnitude greater than the threshold voltage of said liquid crystal means and a frequency greater than the critical flicker fusion frequency of an eye; controlling the duty cycle of said pulses corresponding to desired optical density of said liquid crystal means to maintain the light passing through the lens at a predetermined luminous level and applying said pulses across said liquid crystal means.

8. The method of claim 7, including the step of measuring ambient light intensity, wherein the controlling step includes controlling the duty cycles of said pulses as a function of the ambient light intensity.

* * * * *